(12) United States Patent
Puleo et al.

(10) Patent No.: US 9,063,041 B2
(45) Date of Patent: Jun. 23, 2015

(54) DEVICE AND METHOD FOR DRYING BIOLOGICAL SAMPLE ON SUBSTRATE

(71) Applicant: General Electric Company, Schenectady, NY (US)

(72) Inventors: Christopher Michael Puleo, Niskayuna, NY (US); John Richard Nelson, Cifton Park, NY (US); Patrick McCoy Spooner, Slingerlands, NY (US); Ralf Lenigk, Niskayuna, NY (US)

(73) Assignee: General Electric Company, Niskayuna, NY (US)

( * ) Notice: Subject to any disclaimer, the term of this patent is extended or adjusted under 35 U.S.C. 154(b) by 124 days.

(21) Appl. No.: 13/690,801

(22) Filed: Nov. 30, 2012

(65) Prior Publication Data
US 2014/0154736 A1    Jun. 5, 2014

(51) Int. Cl.
| | |
|---|---|
| B01L 3/00 | (2006.01) |
| B01L 7/00 | (2006.01) |
| G01N 1/30 | (2006.01) |
| G01N 1/40 | (2006.01) |

(52) U.S. Cl.
CPC ............. *G01N 1/30* (2013.01); *Y10T 436/2525* (2015.01); *G01N 2001/4027* (2013.01); *B01L 3/5023* (2013.01); *B01L 3/5088* (2013.01); *B01L 2200/0678* (2013.01); *B01L 2300/0825* (2013.01); *B01L 2300/126* (2013.01); *B01L 2300/1877* (2013.01)

(58) Field of Classification Search
None
See application file for complete search history.

(56) References Cited

U.S. PATENT DOCUMENTS

| | | | |
|---|---|---|---|
| 3,804,077 A | 4/1974 | Williams | |
| 4,751,119 A | 6/1988 | Yukawa | |
| 5,492,837 A * | 2/1996 | Naser-Kolahzadeh et al. | 436/176 |
| 6,248,257 B1 | 6/2001 | Bell et al. | |
| 7,521,246 B2 | 4/2009 | Yang et al. | |
| 7,537,002 B2 * | 5/2009 | Handa et al. | 126/263.01 |
| 7,748,283 B2 * | 7/2010 | Harvey et al. | 73/864.91 |
| 8,203,105 B2 | 6/2012 | Li et al. | |
| 2002/0086346 A1 * | 7/2002 | Ryan | 435/40.5 |
| 2004/0234699 A1 | 11/2004 | Hale et al. | |
| 2006/0115873 A1 | 6/2006 | Peak et al. | |

(Continued)

FOREIGN PATENT DOCUMENTS

| | | |
|---|---|---|
| GB | 2327028 A | 1/1999 |
| WO | 200216383 A1 | 2/2002 |
| WO | 2010106475 A2 | 9/2010 |

(Continued)

OTHER PUBLICATIONS

Search Report and Written Opinion from PCT Application No. PCT/US2013/71949 dated Feb. 12, 2014.

*Primary Examiner* — Allison Fox
(74) *Attorney, Agent, or Firm* — Eileen B. Gallagher (57) ABSTRACT

A method of drying a biological sample disposed on a substrate is provided. The method comprises providing the substrate comprising a sample loading area and a heat source; activating the heat source for generating heat; heating the substrate at least above 65° C.; and drying the biological sample. A device for storing sample is also provided, wherein the device comprises a substrate for biological sample-storage; and a heating component that generates heat to maintain a temperature of at least above 65° C. The heating component may contain one or more reagents, wherein the reagents generate heat to maintain a temperature of at least above 65° C.

24 Claims, 4 Drawing Sheets (56) References Cited

U.S. PATENT DOCUMENTS

2008/0268495 A1* 10/2008 Skold et al. .................. 435/40.5
2010/0065037 A1    3/2010  Root

FOREIGN PATENT DOCUMENTS

| WO | 2010132508 A2 | 11/2010 |
| WO | 2012128702 A1 | 9/2012 |

* cited by examiner

SEQUENCE LISTING

<160> NUMBER OF SEQ ID NOS: 3

<210> SEQ ID NO 1
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1
ttaaagtctc gacggcagaa gcca                                          24

<210> SEQ ID NO 2
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
aacatctttc atcagcttcg cggc                                          24

<210> SEQ ID NO 3
<211> LENGTH: 149
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 3
ttaaagtctc gacggcagaa gccagggcta ttttaccggc gcagtatcgc cgccaggatt    60
gcattgcgca cgggcgacat ctggctggct tcattcacgc ctgctattcc cgtcagcctg   120
agcttgccgc gaagctgatg aaagatgtt                                    149

DEVICE AND METHOD FOR DRYING
BIOLOGICAL SAMPLE ON SUBSTRATE

SEQUENCE LISTING

The instant application contains a Sequence Listing which has been submitted in ASCII format via EFS-Web and is hereby incorporated by reference in its entirety. Said ASCII copy, created on Nov. 28, 2012, is named 260600.txt and is 1,099 bytes in size.

FIELD OF THE INVENTION

The invention generally relates to methods for drying biological samples on a substrate for preservation and a device for drying and preserving biological samples.

BACKGROUND

Biological sample storage and preservation is desired as the preserved sample can be used for various applications, such as analyte detection, sensing, forensic and diagnostic applications, genome sequencing, whole-genome amplification, and the like. The sample storage and preservation require sample drying on a substrate.

Some of the currently used devices for preservation of samples on paper substrates are available. For example, a buccal cell sampling device, wherein the sample is dried on a substrate under ambient conditions. The sample drying using such device may be a slow process, particularly at high humidity. Porous or non-porous substrates are commonly used for preservation of biological samples, such as paper cards or membranes. Examples of paper cards or membranes include chemically treated FTA® and FTA®Elute papers (GE Healthcare) for preservation of nucleic acid samples, and the FTA®DMPK cards and 903® cards (GE Healthcare) for preservation of blood samples. The substrates employed a method of absorption and drying of a wet biological sample, such as blood, buccal swabs or macerated tissue disposed on the substrate, however the drying process is time consuming. An incomplete or slow drying affects the stability of the sample and that may generate inconsistent results in subsequent analyses of the preserved samples. The time consuming method of drying a sample limits application of the substrate to use in a lab facility or other time sensitive applications.

A number of portable heat sources, particularly for applications to the heating of food are known. The portable heat sources have a number of disadvantages, including the low efficiency and formation of flammable and/or toxic by-products that may be harmful for biological samples. Chemical heat pads or chemical heaters are also known to evaporate various solvents, however the chemical heaters employ corrosive chemicals, for example, the reaction of sodium hydroxide with hydrochloric acid.

A substrate with a heat source, which is safe during operation, storage and transport, convenient to use and efficient to generate required heat for biological sample drying is highly desirable. Accordingly, there is a need for a method and a device that dries a biological sample in a minimal time without affecting the quality of the sample for subsequent storage and analysis.

BRIEF DESCRIPTION

One embodiment of a method of drying a biological sample disposed on a substrate comprises providing the substrate comprising a sample loading area and a heat source; activating the heat source for generating heat; heating the substrate at least above 65° C.; and drying the biological sample.

In another embodiment, a method of drying a biological sample, comprises disposing the biological sample on a substrate, wherein the substrate comprises a sample loading area and a reactor component comprising one or more reagents; activating the one or more reagents to initiate an exothermic reaction; heating the substrate at about 95° C.; and drying the biological sample disposed on the substrate in less than about 2 minutes.

In yet another embodiment, a device comprises a substrate for biological sample-storage, wherein the substrate comprises a sample loading area; and a heat source that generates a heat to maintain a temperature of at least above 65° C.

DRAWINGS

These and other features, aspects, and advantages of the present invention will become better understood when the following detailed description is read with reference to the accompanying drawings in which like characters represent like parts throughout the drawings, wherein.

DETAILED DESCRIPTION

The invention is directed to methods and devices for drying biological sample for preservation or storage. The present methods allow drying of a biological sample disposed on a substrate comprising a sample loading area and a heat source. The methods generally comprise activating the heat source present on the substrate for generating heat, heating the substrate followed by drying the biological sample disposed on the substrate. The methods utilize controlled heating of the substrate at high temperature to accomplish sample drying in minimal time without affecting the sample.

To more clearly and concisely describe and point out the subject matter of the claimed invention, the following definitions are provided for specific terms, which are used in the following description and the appended claims. Throughout the specification, use of specific terms should be considered as non-limiting examples.

The singular forms "a", "an" and "the" include plural referents unless the context clearly dictates otherwise. Approximating language, as used herein throughout the specification and claims, may be applied to modify any quantitative representation that could permissibly vary without resulting in a change in the basic function to which it is related. Accordingly, a value modified by a term such as "about" is not to be limited to the precise value specified. In some instances, the approximating language may correspond to the precision of an instrument for measuring the value. Where necessary, ranges have been supplied, and those ranges are inclusive of all sub-ranges there between.

Unless otherwise indicated, all numbers expressing quantities of ingredients, properties such as molecular weight, reaction conditions, so forth used in the specification and claims are to be understood as being modified in all instances by the term "about." Accordingly, unless indicated to the contrary, the numerical parameters set forth in the following specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques.

As used herein, the term "activating" refers to initiation of a process, such as to start a chemical reaction or an electrochemical reaction on a substrate using an activation component. The activation may be accomplished physically, chemically, electrically or mechanically. For example, addition of one or more reagents or solvents to the reagents present on the substrate is an activation process, wherein the added reagent or solvent initiates the reaction. An example of mechanical activation includes, initiation of a reaction using a mechanical component, such as a pulling tab attached to a pouch contains a reagent or solvent. On operating the pulling tab, the pouch releases the reagent or solvent to the substrate and the contact of the more than one reagents starts the reaction.

As used herein, the term "substrate" means a matrix, a fibrous web, a membrane, or a foam. The substrate may comprise fibres, e.g. cellulose or glass fibres, and optionally other components, such as e.g. particulate fillers, wet strength additives or dry strength additives or retention agents. Substrate may also comprise reagents for preservation of biological sample components, lysis of cells or biomolecule stabilizing agents.

One embodiment of a method comprises providing a substrate, wherein the substrate comprises a sample loading area and a heat source, activating the heat source for generating heat, heating the substrate at least above 65° C. and drying the biological sample disposed on the substrate.

As noted, the substrate comprises a sample loading area and a heat source. The heat source may comprise a reactor component comprising one or more reagents, an electric heater, an infra-red (IR) heater or combinations thereof. The substrate may further comprise an activation component. The substrate may be described in detail with reference to the device and FIGS. 1A-C.

In one or more embodiments, the activation is executed mechanically, physically, chemically, electrically or combinations thereof. If the heat source is a reactor component comprising one or more chemical reagents, the reagents may be activated by addition of one or more chemical reagents or solvents to start an exothermic phase transition, chemical or electrochemical reaction. In some embodiments, the reagents are not reusable and do not have a well-defined maximum temperature. If the heat source is an electrical heater, then an electrical switch or connection may result in an activation of the heater followed by heat generation. In some other embodiments, the activation is executed by using a pulling tab, a switch, a slit disc, a lever or a spring.

In one or more embodiments of the reactor component, the reagents are activated by hydration of the reagents on the substrate, aeration of the reagents present on the substrate or contact of one or more reagents or solvents. The contact of one or more reagents may start the reaction, wherein more than one reagents are present on the substrate, placed on a distant location or stored in two or more different chambers or pouches. The contact of the reagents may also occur when one or more reagents added from outside of the substrate.

In one embodiment, the reagents are activated by hydration. In this embodiment, water is added to the reagents to start an exothermic reaction. The exothermic reaction generates a heat in a controlled manner while the addition of water is controlled. In one example of hydration, when a substrate comprises CaO, hydration results in exothermic reaction generating heat that is sufficient to dry the biological sample disposed on the substrate.

In some other embodiments, the reagents are activated by aeration. For example, a substrate containing iron powder and a salt solution, wherein the iron powder is activated by an access of atmospheric oxygen to start oxidation of the iron, results in an exothermic reaction.

In some embodiments, the reagents are activated by an activation component which is a mechanical component. The mechanical component includes, but is not limited to, a slit disk, a spring, a switch, a knob, a lever and a pulling tab. For example, one or more reagents are activated by bending a slit metal disk, pulling a metal spring, pulling a tab or by operating a switch. In one example, the user pulls a tab to initiate an exothermic reaction. The heat generated by the exothermic reaction evaporates the solvent from the sample results in instant drying of the biological sample on the substrate. In an exemplary method, a supersaturated salt solution is used as reagents and a metal spring bends or twists inside the solution of super saturated salts to start the crystallisation of the salt. The crystallisation results in heat generation till the completion of the exothermic reaction.

In one or more embodiments, the heat is generated by a reaction between reagents that are brought into contact with each other. The addition of one or more reagents or solvents activates the reagents present on the substrate. The addition of reagents initiates the reaction. For example, a substrate containing a magnesium/iron (Mg/Fe) alloy that is activated by providing an electrolytic solution to start an exothermic reaction.

As noted above, the substrate is heated at least above 65° C. In some embodiments, the substrate is heated on activation and reaches a temperature, which is in a range of 65° C. to 95° C. The substrate may maintain a temperature for at least about 5 min. The substrate may maintain a temperature for about 60 min. A temperature profile for drying a substrate may be "tailored", depending on the application requirement. The temperature of the substrate may be measured by placing a substrate on a bench top at room temperature, placing a thermometric transducer on the top of the substrate, activating the substrate and recording the temperature.

In some embodiments, the substrate is heated at 95° C., wherein the incubation of the substrate for less than 5 minutes is sufficient to dry the biological sample disposed on the substrate. In one embodiment, the substrate is heated at 95° C., wherein the incubation of the substrate for less than 1 minute to dry the biological sample disposed on the substrate. The drying of a biological sample in a shorter time, such as for less than 2 minutes, may be useful in a number of growth areas which require fast processing including, drug metabolism and pharmacokinetics (DMPK), rapid human identification (Rapid HID), rapid point of care analytical platforms or field-based sample collection. The present method is interchangeably used herein as a "quick drying method". The quick drying method eliminates the time consuming part of the currently known method using a substrate, such as an FTA® card, wherein the drying time is generally more than an hour. The time consuming drying step in the presently used FTA® process flow precludes the use of FTA® technology in the field-based sample collection, DMPK applications and rapid point-of-care analytical devices.

Figure 2:
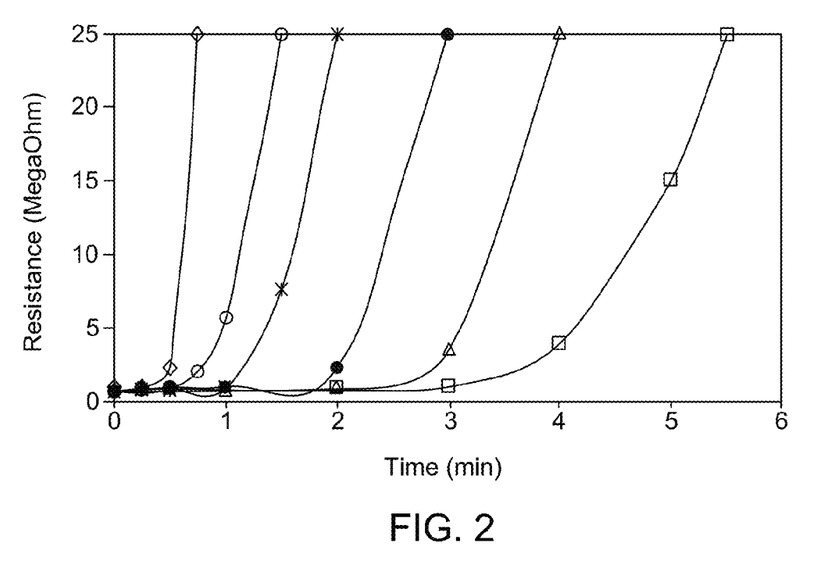
FIG. 2 provides a series of graphs showing efficient drying of bacterial growth media applied to 31ETF paper at different temperatures.

In some of the examples, the drying time was measured (FIGS. 2-3) at different temperatures, and the optimum drying time was determined (FIGS. 4-5) as less than 2 minutes at about 95° C. The heating of the substrate at 95° C. for 2 minutes is sufficient to dry the sample. Moreover, different experimental results (FIGS. 4 and 5) ensure that quick drying method at such high temperature (95° C.) does not affect nucleic acid amplification and bacteria lysis. The quick drying method employs a high temperature incubation for a short duration of time, such as 95° C. for 1 minute, which does not affect the integrity of the biological molecules, like nucleic acids. In one example, the drying for less than 45 seconds is sufficient at 95° C. (FIG. 2). The quick drying method of the sample is advantageous, as that prevents degradation of the components present in the sample. Many proteases and nucleases are inactivated by incubation at high temperature, which reduces the degradation of the components. A heating step at 65° C. is commonly used for heat inactivation of enzymes used in many molecular biology applications, which further ensures the stability of the component.

Figure 1A:
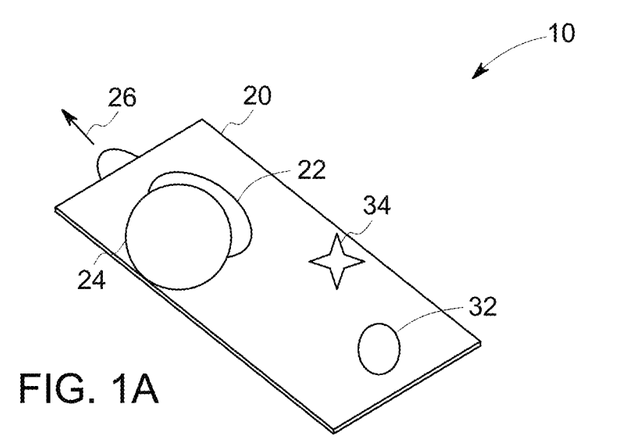
FIGS. 1A-C are schematic representations of a device for biological sample storage.

In one or more embodiments, heat treatment to a sample disposed on a substrate results in evaporation of a solvent present in the sample. The evaporation further results in sample drying. In certain embodiments, the moisture content of the biological sample decreases on heating. For example, FIG. 1 shows the moisture content of the biological sample, based on electrical resistance measurements through the liquid sample, drops to near 0 within one minute after heating at 95° C. In some embodiments, if the substrate itself is wet, the moisture content of the substrate also decreases during quick drying process. For sample drying, the use of dry substrate is desirable. Use of dry substrate or adjacent desiccating materials may further reduce the time of the sample drying, by removing water vapour produced upon sample heating.

The sample drying time may be minimized by placing the heat source in contact with the substrate. In one embodiment of the quick drying process, a short drying time, e.g. 2 minutes, may be sufficient when the heat generating component is placed in contact with the substrate. A longer time, up to about 10 min, may be needed when the heat source is placed adjacent to a plurality of the substrates. The size and character of the heat generating component can be selected to provide suitable duration of the heating.

Overheating of any heat-sensitive sample components may be avoided by controlling the heat generation. For example, a maximum temperature reached by a substrate may be controlled to avoid the risk of overheating. In one or more embodiments, the method further comprises regulation of a heating step by controlling the exothermic reaction. The controlled heating and maintenance of temperature may prevent the degradation of the sample that comprises heat-sensitive components.

In one or more embodiments, generation of heat may be controlled by controlling the rate of addition of a solvent or a reagent to the substrate. For example, a rate of addition of water to the substrate comprising CaO is controlled and may be modified to decrease or increase the rate of reaction depending on the heat required per minute. In another embodiment, a rate of addition of a second reagent or a solvent to a substrate-bound first reagent is controlled by using a syringe, a pump, a valve, a conduit or a combination thereof. A pouch with multiple pores may also be used to add air, solvent or reagent solution to the substrate. In some embodiments, flow rate of a fluid or gas to the substrate-bound reagents is controlled by using an appropriate conduit, utilizing a mass flow rate to control the rate of the exothermic reaction. The concentration of the reagent present in the reactor component may be modified depending on the requirement of the amount of heat. In one embodiment, a concentration of a reagent is optimized such that the reagent generates an amount of heat, which dries the sample 95° C. in as little as 1 minute.

The dried sample may be extracted or eluted from the substrate using various techniques. Different buffer solutions or pure solvents may be used to elute the sample from the substrate. The elution process may include washing of the substrate with a buffer. For some non-paper substrate, the elution may be achieved by increasing the concentration of salt in the buffer solution, while using a batch-wise elution or chromatographic separation. The elution process may also comprise electrophoresis, elution using a pump/fluid or elution using a fluid flow combined with various means of mechanical or electric agitation.

In some embodiments, the method further comprises analysing at least one component of the biological sample disposed on the substrate, after drying. The analysis may involve e.g. mass spectrometric analysis, immunoassays of proteins, polymerase chain reaction (PCR) or other similar interrogation methods for analysis of nucleic acids and gel electrophoresis of proteins or nucleic acids. The analysis may result in detection of specific nucleic acid sequences, detection of a particular protein or peptide sequence, or identification of a mutant species.

In one or more embodiments, the biomolecules comprise proteins, peptides, nucleic acids or combinations thereof. In one embodiment, the biomolecules comprise nucleic acids. In some embodiments, the nucleic acids isolated from the biological material include deoxyribonucleic acids (DNAs) or ribonucleic acids (RNAs). In one embodiment, the nucleic acid is deoxyribonucleic acids (DNAs). In one or more embodiments, the DNA may be a genomic DNA, chromosomal DNA, bacterial DNA, plasmid DNA, plant DNA, synthetic DNA, a recombinant DNA, an amplified DNA and combinations thereof.

In one or more embodiments, a device comprises a substrate for biological sample-storage, and a heat source that generates heat to maintain a temperature of at least above 65° C.

In one or more embodiments, a substrate comprises a solid phase extraction matrix, a filtration matrix, a paper, a foam, a membrane or combinations thereof. In some embodiments, the substrate comprises a polymeric material. In some embodiments, the substrate is a polymeric foam or membrane.

In some embodiments, the substrate may comprise a plurality of pores. For example, the substrate comprises a sheet of porous material, such as a paper. Paper may be a convenient material to use as a substrate, as paper has suitable absorption properties and mechanical properties. Papers comprising cell-lysis or biomolecules preservation reagents, are often more hygroscopic than plain papers. The method and device may be particularly advantageous when such hygroscopic papers are used.

As noted, the substrate comprises a sample loading area and a heat source. In some embodiments, the substrate comprises an embossed area for loading a sample. The substrate may further comprise a printed or coloured area for sample loading. In some embodiments, the area may further comprise an identifying code, e.g. in the form of a number, a bar code or an RFID tag. The sample loading area may comprise a cap which protects the area after loading. The cap also protects the sample after drying.

The heat source may be a reactor component, an IR heater or an electric heater. In some embodiments, the heat source is a reactor component. In some embodiments, the heat source comprises a reactor component comprising one or more reagents, wherein the reagents generate heat upon addition of other reagents or solvents. In one or more embodiments, the reactor component comprises one or more reagents, wherein the reagents are impregnated in the substrate. In some aspects, the substrate is devoid of embedded reagents and the reagents may be added from outside to the substrate before use. In some embodiments, the reagents may be packaged in a pouch, bag or envelope, and housed on the substrate. The dried reagents may be embedded in the substrate, wherein the reagents need to be hydrated before use.

The heat may be generated by exothermic reaction of a reagent and a solvent, more than one reagent, more than one reagent and a solvent or solution, or more than one reagent with more than one solvent or solution. In some embodiments, the one or more reagents comprise an acidic salt, a basic salt, an acidic anhydrite, a basic anhydrite or combinations thereof.

In one or more embodiments, the reactor component is in direct or indirect contact with the substrate. In some embodiments, the reactor component is positioned at a distance from the substrate, for example the reactor component is placed at a distance of less than about 10 mm, such as less than about 2 mm from the substrate. A short distance between the heat source and the sample loading area facilitates efficient heat transfer and sample-drying. In certain embodiments, the reactor component is positioned in contact with the substrate. The reactor component, if so desired, may be positioned in contact with the substrate. In some embodiments, the heat source and sample loading area are placed on opposite side of the substrate to reduce the risk of sample contamination. It is also possible to position a protective film between the reactor component and the substrate to further reduce a contamination risk. In this case, the reactor component may be in indirect contact with the substrate via a protective film.

In some embodiments, the substrate comprises at least one reagent for lysis of the cells, wherein the cells are disposed on the substrate as a biological sample. In some embodiments, cell lysis may be accomplished using, e.g. surfactants or chaotropes. Examples of such substrates are non-modified papers such as 903® or 31ETF® (GE Healthcare) and papers with lysing/preservation reagents such as FTA®, FTA DMPK® and FTAElute® (GE Healthcare).

In some embodiments, the substrate comprises at least one reagent for stabilization of the components present in the biological sample. The reagents may increase the stability of certain inherently unstable components, e.g. complexing agents and/or radical scavengers are used as stabilisers for nucleic acids. For example, polyhydric compounds such as sugars or polyvinyl alcohol provide stabilising effects for proteins. In some embodiments, the substrate comprises at least one reagent for lysis of the cells, wherein the biological sample disposed on the substrate is a sample of live cells.

In one or more embodiments, the substrate further comprises cell lysis reagents and biomolecule stabilizing reagents. As noted, lysis of cells can be accomplished with e.g. surfactants or chaotropes. The substrate with cell-lysis reagents is also desirable to have stabilization agents for biological sample, which may be useful for stabilising the biomolecules for further analysis. For example, the cells are lysed by cell-lysis reagents, which results in extraction of proteins or nucleic acids, which are stabilized by the stabilization reagents. In some embodiments, the stabilization reagents are for nucleic acid stabilization, or in some other embodiments, the stabilization reagents are for protein stabilization. An example of a substrate comprising a stabilization reagent and a cell-lysis reagent is an FTA® card.

A thickness of the substrate having a dimension of less than 1 mm may be desirable. The drying of a biological sample disposed on the substrate may be faster, wherein the substrate is a thin substrate. In one or more embodiments, the substrate may have a thickness less than 1 mm, such as 0.3-0.7 mm. The evaporation of the solvent present in the sample or in the substrate may be expedited while the thickness of the substrate is less. In one or more embodiments, the substrate has a thickness between 20 microns to 5 mm.

The substrate may be in a card format, self-supported or encased in a frame. In some embodiments, the substrate is self-supported, wherein a hard case or frame is embedded within the substrate. In some examples, a paper substrate is hardened by adding an adhesive. The substrate may comprise fibres, e.g. cellulose or glass fibres, and optionally other components, such as particulate fillers, wet strength additives or dry strength additives or retention agents. In some other embodiments, the substrate is encased in a frame.

In some embodiments, the device further comprises one or more controllers, wherein the controllers control the temperature of the substrate by regulating the rate of the reaction. The reaction rate may be controlled by controlling a flow of a fluid which is added to the substrate. The controller may further regulate a rate of addition of one or more reagents or solvents to the substrate.

In one embodiment, the device is operationally controlled by a controller for drying the biological sample. In some embodiments, a controller operationally couple to the device and controls various functions of the device. For example, while a device is automatic; a controller controls various functions of the device and operated independently. In one embodiment, the device comprises a controller to maintain a constant fluid flow by regulating a valve or pump. In some embodiments, the valve itself regulates the fluid flow. In one embodiment, the controller controls the overall device to operate, wherein the device is automated. The controller may further be pre-programmed before operation, depending on the application requirement or user requirement. The controller may comprise a micro controller circuit, wherein the controller may be a digital controller.

To maintain a constant temperature during drying of the biological sample, a temperature sensor may be useful. In one or more embodiments, the device further comprises one or more temperature sensors. If the temperature changes during drying process, the sensor may provide a signal and the heating process may be modified to maintain the constant temperature. The temperature of the substrate may be increased or decreased depending on sensor signal. When the temperature of the substrate is higher or lower than the expected temperature, the sensor automatically sends a signal to a temperature controller to control the temperature of the device. The device may be pre-programmed as per user requirement.

Figure 1B:
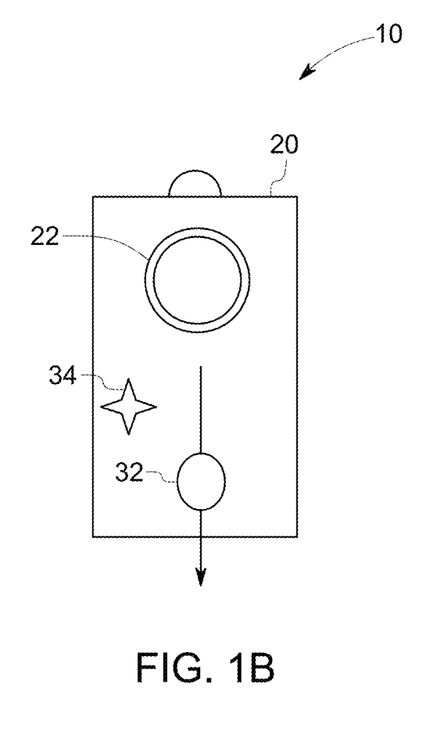
Figure 1C:
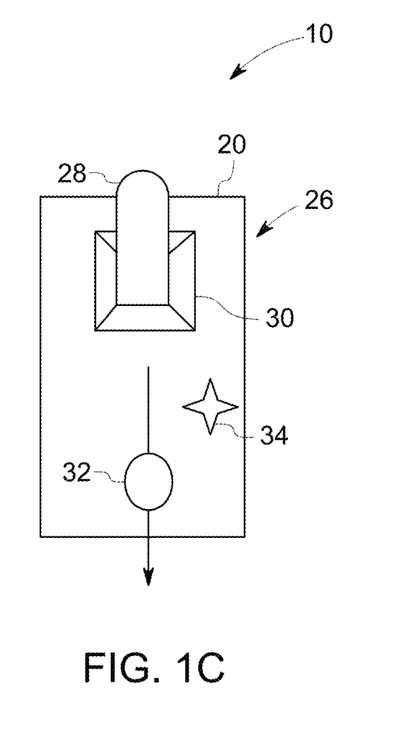

FIG. 1A is a schematic drawing of non-limiting examples of an overall device structure 10. FIGS. 1B and 1C are two more schematic drawings to show front view and back view of the device. FIGS. 1A-C show various parts embodied in the device 10, such as a substrate 20, a sample loading area 22 and a heat source 26. The sample loading area 22 present on one side of the substrate 20. For example, the sample loading area is on the front side of the substrate, wherein the heat source 26 is on the opposite side of the substrate. In some embodiments, the device may further comprise a cap 24, which may cover the sample loading area or surface of the entire substrate.

As illustrated in FIGS. 1A-C, in one or more embodiments of the device 10, the heat source 26 is a reactor component comprises one or more reagents to generate heat. In some other embodiments, the heat source 26 is an electric heater, such as a heat pad, or a hot plate. In yet another embodiment, the heat source is an infra-red (IR) heater, wherein the source of heating is IR rays. In one or more embodiments of the device, the heat source 26 may be present on the substrate, either on the same side comprising the sample loading area 22 or on the other side of the substrate 20.

In some embodiments of the device 10 (as shown in FIG. 1C), the heat source may be activated or initiated by an activation component 28. In certain embodiments, the activation component 28 is capable of activating the reactor component. The activation component 28 may be a slit disk, a spring, a switch, a knob, a lever or a pulling tab. In one or more embodiments, the heat source is a reactor component 26, which comprises one or more reagents and the reactor component comprises a pulling tab 28 as an activation component. The pulling tab 28 is used to initiate the exothermic reaction. In some embodiments, the activation component 28 may be a protrusion on or adjacent to the substrate, wherein the activation component 28 causes a slit metal disk or spring to bend upon positioning of the component to initiate the reaction for generating heat. The slit metal disk or spring may be located at a specific position in the reactor component, such as in a corner of the component. The activation component 28 facilitates the activation of the heat source 26 without touching the source. The time between the activation and positioning of the activation component may be shortened.

As noted, the solvent or reagent is added to the substrate 20 from outside manually, using a syringe or a pipette. In some embodiments of the device 10, the reactor component 26 is operationally coupled to a conduit through which the solvent or reagent is added to the substrate 20 to initiate the reaction. In some embodiments, a buffer or water is added to the substrate using a syringe, a pipette, or a conduit. In some embodiments, the device 10 is operationally coupled to a pump, wherein the addition of reagents may be controlled using the pump. In one or more embodiments, a port is further coupled to a reservoir comprising a solvent, such as water. The water from the reservoir is supplied to the substrate 20 for initiation of the reaction, followed by drying, as per application requirement.

In one or more embodiments, the device further comprises a controller 32 (FIGS. 1A-C). In some embodiments, the controller 32 may be a valve that controls the fluid flow. In one embodiment, the controller 32 controls the overall device 10 operation, wherein the controller 32 is a switch for operating the device 10 when the device is automated. The controller 32 may further be pre-programmed before the operation depending on the application requirement. The controller 32 may comprise a micro controller circuit, wherein the controller may be a digital controller.

In some embodiments, as illustrated by FIG. 1C, the reactor component is placed on a holder 30. The holder 30 may be placed at the centre of the substrate 20 or may be moveable towards the end of the substrate 20. In some embodiments, as the holder 30 is movable type, the distance between the heating source 26 and the sample loading area 22 may be increased or decreased. In these embodiments, the heating source 26 may conveniently be activated and immediately placed in contact with or at a close distance from the sample loading area 22 of the substrate 20. The activation component 28 may be present on or adjacent to the substrate holder 30.

As illustrated in FIGS. 1A-C, the device further comprises one or more temperature sensors 34. In one or more embodiments, a temperature sensor 34 maintains a constant temperature during the drying process on the substrate 20. In some embodiments of the device, the temperature sensor 34 sends a signal to the controller, if the temperature needs to be changed or controlled during the drying process. The temperature sensor 34 may also send a different signal when the temperature is constant and the device does not require any further action for changing the temperature. Depending on the signal received from the sensor 34, the rate of generating heat may also be modified, such as either increases to maintain optimum temperature or decreases to avoid overheating the sample.

In some embodiments, the device 10 may further comprise a moveable sample collection chamber. This moveable sample collection chamber may be situated near the sample loading area 22 of the substrate 20. The collection chamber may be movable and may bring into contact with at least a portion of the substrate 20. The moveable sample collection chamber may e.g. be attached to a hinged arm.

In some embodiments, the device is housed in a system for further downstream applications. The system may comprise air vents in connection with air channels, wherein the air channels may be present on or adjacent to the substrates. In one or more embodiments, the housing may be configured to hold a plurality of substrates, wherein several samples may be applied to different substrates. In these embodiments of the system, more than one sample, either same or different, may be rapidly dried in one operation. The air vents on the system may be aligned with the air channels to obtain an efficient convective heat transfer from the heat source. The heat source may be positioned below the substrate to improve the convection. The substrates may be positioned perpendicular or inclined to the length axis of the heat source. The substrate holder 30 may hold the substrates 20, e.g. in the format of plastic framed paper cards. The substrates 20 may be used to collect sample blood from animals or humans during e.g. drug metabolism and pharmacokinetics (DMPK) testing of drug candidates. The substrate may be transported to a central analysis facility for analysis of the dried blood spots.

In some embodiments, the device may also contain stored desiccating materials positioned near the substrate. The desiccating materials may aid in removing water vapour from the local environment around the substrate, and thus further aid in substrate drying during heating. This embodiment may be significant in reducing the quick heating time (<1 minute) across all product environments, including humid areas.

The biological sample may be dried and stored on the substrate for at least 24 hrs. The substrate with dried sample may be transported to a central facility for analysis. The sample storage in a small field-able device for at least 24 hrs provides a facility of storing the sample and use for any downstream applications as required. The quick drying process also prevents degradation of the biological sample. The rapid and reproducible drying of the sample even under difficult conditions, leading to better sample recoveries and improved robustness.

EXAMPLE

Materials

The substrates used for the experiments include 903® or 31ETF® (GE Healthcare) and papers with lysing/preservation reagents such as FTA®, FTA DMPK® and FTAElute® (GE Healthcare). Illustra™ spin column (from GE Healthcare) was used for testing various matrices, reagents, buffers, and standardizing nucleic acid purification protocol. Illustra PuRe Taq Ready-to-Go™ PCR beads (from GE Healthcare) was used for DNA amplification using PCR.

Example 1

Dryness Measurement Tested Via Electrical Conductance

The liquid sample of bacterial growth media (LB growth media) was disposed on a series of FTA® substrates and the substrates were dried by exposure to air while the substrate was heated at different temperatures. The conditions for quick drying was determined by comparative analysis of sample dryness at different temperatures, such as 45° C., 55° C., 65° C., 75° C., 85° C. and 95° C. The dryness of the substrate was measured using electrical resistance, as measured by a hand-held multimeter. FIG. 2 shows that drying time for a biological sample, in this case a bacterial growth media, increases with decrease in temperature. The sample was dried at 95° C. for less than about 1 minute, such as for about 30 seconds.

An Ohm-meter with the range set to 20 MΩ was used to determine the dryness of the membrane. The 2 measuring tips were held 3 mm apart and were pressed against the membrane without piercing it. Once a reading could no longer be obtained (resistance>20 MΩ), the membrane was considered dry.

Figure 3:
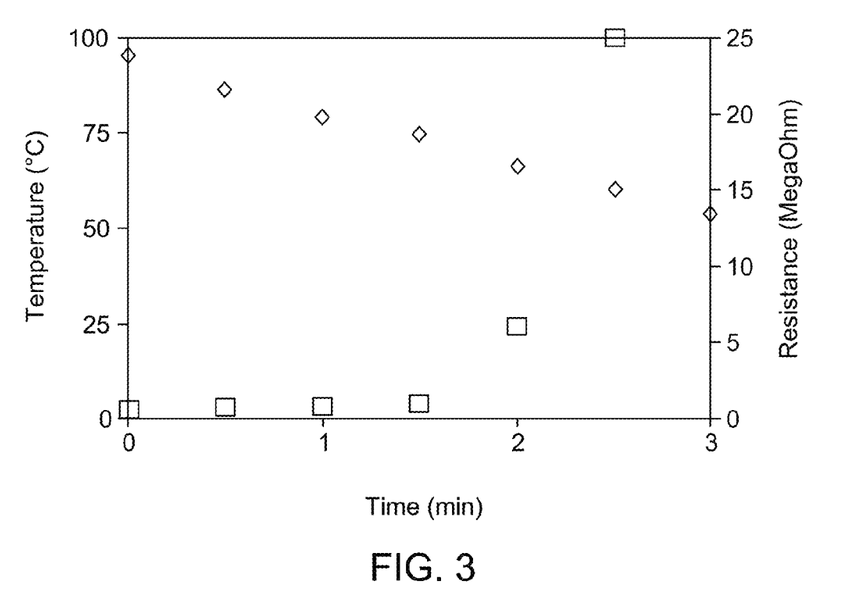
FIG. 3 provides two graphs showing temperature profiles measured at the surface of an exothermic reaction pouch for drying of a biological sample.

For this experiment, a 31-ETF® substrate with a pouch containing 0.5 g of CaO powder and an adjacent pouch containing water was employed. 0.5 mL of water was added to the CaO and mixed to initiate the reaction. The water was added by breaking a foil separation tab present between the two pouches, which removed the separation wall and helped in mixing the materials of the two pouches. FIG. 3 curve with diamonds shows a temperature profile of this exothermic reaction. The 31-ETF® substrate was placed directly on top of the foil reaction pouch at peak temperature (~95° C.), which results in drying the sample as shown in FIG. 3 curve with squares. The curve 42 of FIG. 3 (diamonds) may be compared to the curves of FIG. 2, which determine the holding time of the sample at a particular temperature.

Example 2

Amplification of Sample Followed by Drying at 95° C. for 2 min

In another experiment, an E. coli specific PCR was performed using DNA extracted from an E. coli sample loaded on the substrate (6 uL sample). In this case, the E. coli cell extract was loaded on two types of the substrates, 31-ETF® and FTA® (4 mm punch). The E. coli samples were amplified directly from paper using the method described above. The PCR was performed using Illustra PuRe Taq Ready-to-Go™ PCR beads using E. coli specific primers (SEQ. ID. No 1: 5' TTAAAGTCTCGACGGCAGAAGCCA 3' and SEQ. ID. No 2: 5' AACATCTTTCATCAGCTTCGCGGC 3'). In the PCR, one amplicon was employed having SEQ. ID. No 3: 5'-TTAAAGTCTCGACGGCAGAAGCCAGGGC-TATTTTACCGGCGCAGTATCGCCG CCAGGATTGCAT-TGCGCACGGGCGACATCTGGCTGGCT-TCATTCACGCCTGCT ATTCCCGTCAGCCTGAGCTTGCCGC-GAAGCTGATGAAAGATGTT-3'.

Figure 4:
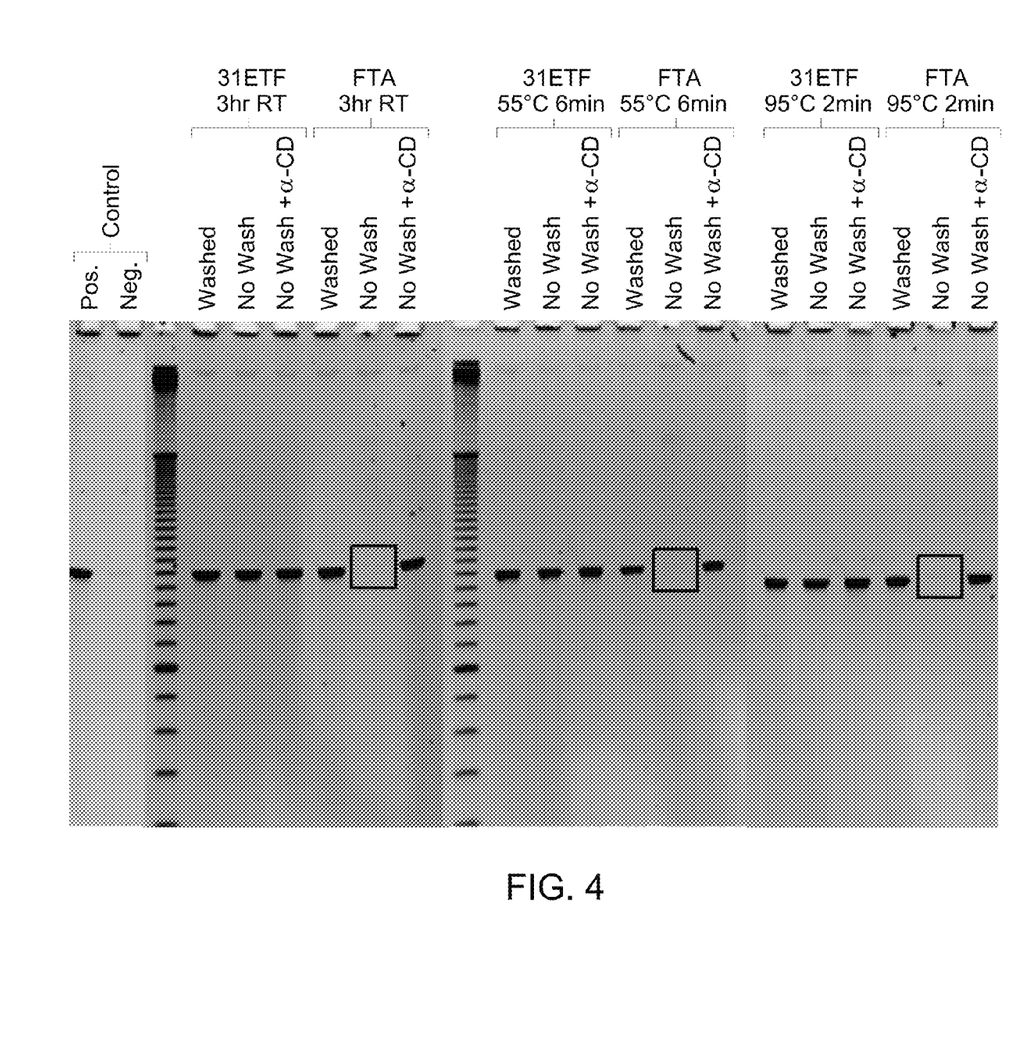
FIG. 4 provides an image of gel electrophoresis showing the DNA amplification products generated from nucleic acids stored on the sample collection substrates after drying at different temperatures, such as at room temperature, 55° C. and 95° C. using 31 ETF® and FTA® paper substrates.

In FIG. 4, lane 1 shows a band for DNA isolated from E. coli as positive control and lane 2 is devoid of any band, as buffer was loaded as negative control. Lane 3 shows DNA ladder with different molecular weight DNA, wherein lanes 4, 5 and 6 show sample eluted from 31-ETF® substrate after washing, without washing and without washing in presence of α-cyclodextran respectively, while incubated at room temperature for 3 hrs. Lanes 7, 8 and 9 show samples eluted from FTA® substrate after washing, without washing and without washing in presence of α-cyclodextran respectively, while incubated at room temperature for 3 hrs. Lane 10 shows DNA ladder with different molecular weight DNA, wherein lanes 11, 12 and 13 show samples eluted from 31-ETF® substrate after washing, without washing and without washing in presence of α-cyclodextran respectively, lanes 14, 15 and 16 show sample eluted from FTA® substrate after washing, without washing and without washing in presence of α-cyclodextran respectively, while incubated at 55 C for 6 minutes. Lanes 17, 18, and 19 show samples eluted from 31-ETF® substrate after washing, without washing and without washing in presence of α-cyclodextran respectively, lanes 20, 21 and 22 show sample eluted from FTA® substrate after washing, without washing and without washing in presence of α-cyclodextran respectively, while incubated at 95° C. for 2 minutes. Lanes 8, 15 and 21 do not contain any band at room temperature, 55° C. and 95° C. respectively for the sample eluted without wash and without α-cyclodextran. Therefore, amplification of nucleic acids from a biological sample is not inhibited by drying the sample even at 95° C.

Example 3

Lysis of E. coli During Quick Drying

Figure 5:
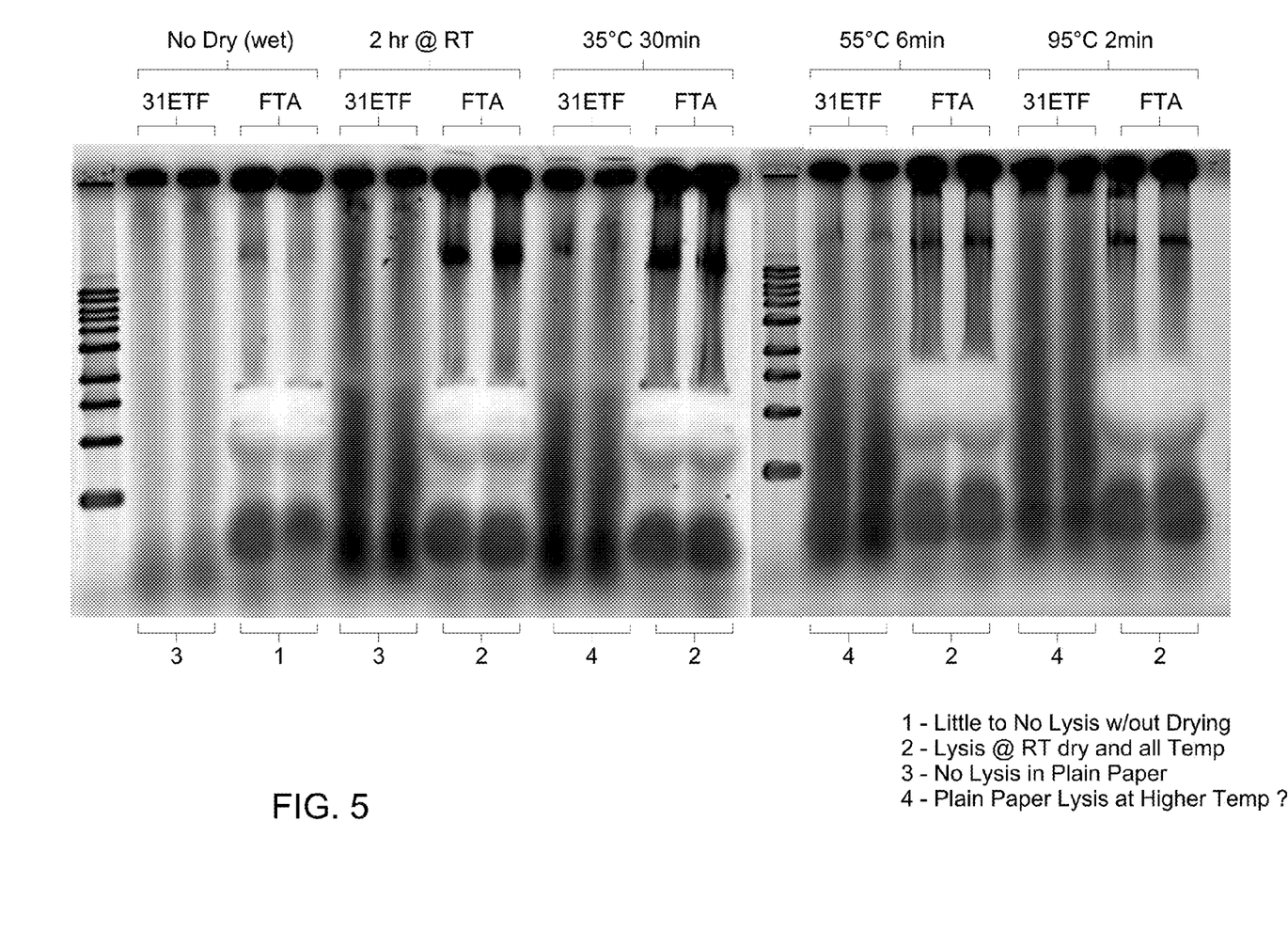
FIG. 5 provides an image of gel electrophoresis showing the DNA electrophoretically extracted from the *E. coli* sample loaded on the substrates after lysis at different temperatures, such as at room temperature, 35° C., 55° C. and 95° C. using 31 ETF® and FTA® paper substrates.

A 6 uL sample from an overnight E. coli culture was loaded on to the 31 ETF and FTA substrates. The experiment was performed for the E. coli sample without drying, drying at room temperature for 2 hrs, drying at 35° C. for 30 minutes, drying at 55° C. for 6 minutes and drying at 95° C. for 2 minutes. In FIG. 5, lane 1 shows DNA ladder with different molecular weight DNA. Lanes 2 and 3 are devoid of any bands as there was no lysis of E. coli cells in plain paper, 31 ETF. Lanes 4 and 5 are showing faint bands as a portion of E. coli cells were lysed immediately on FTA paper without drying. Lanes 6 and 7 are devoid of any bands as there was no lysis of E. coli cells in plain paper even after drying at room temperature for about 2 hrs. Lanes 8 and 9 show bands as E. coli cells were lysed on FTA paper after drying at room temperature for about 2 hrs. Lanes 10 and 11 show bands as E. coli cells were lysed on plain paper (31 ETF) after drying at 35° C. for about 30 minutes. Lanes 12 and 13 also show bands as E. coli cells were lysed FTA after drying at 35° C. for about 30 minutes. Lane 14 shows DNA ladder with different molecular weight DNA. Lanes 15 and 16 show bands as E. coli cells were lysed on plain paper (31 ETF) after drying at 55° C. for about 6 minutes. Lanes 17 and 18 show bands as E. coli cells were lysed on FTA after drying at 55° C. for about 6 minutes. Lanes 19 and 20 show bands as E. coli cells were lysed on plain paper (31 ETF) after drying at 95° C. for about 2 minutes. Lanes 21 and 22 show bands as E. coli cells were lysed on FTA after drying at 95° C. for about 2 minutes. Therefore, E. coli cells are lysed during quick drying at 95° C.

While only certain features of the invention have been illustrated and described herein, many modifications and changes will occur to those skilled in the art. It is, therefore, to be understood that the appended claims are intended to cover all such modifications and changes as fall within the true spirit of the invention.

The invention claimed is:

1. A method of drying a biological sample disposed on a substrate, comprising:
   providing the substrate, wherein the substrate comprises a sample loading area and a heat source;
   disposing the biological sample on the substrate;
   activating the heat source for generating heat;
   heating the substrate at least 65° C.; and
   drying the biological sample.

2. The method of claim 1, wherein the substrate is heated at a temperature in a range of 65° C. to 95° C.

3. The method of claim 1, wherein the substrate is heated for less than 5 minutes.

4. The method of claim 1, wherein the substrate is heated for less than 1 minute.

5. The method of claim 1, wherein the substrate is heated at about 95° C. for 2 minutes.

6. The method of claim 1, wherein the heat source comprises a reactor component comprising one or more reagents, an electric heater, an infrared heater or combinations thereof.

7. The method of claim 1, wherein the reactor component comprises one or more reagents.

8. The method of claim 7, wherein the one or more reagents generate heat by exothermic reaction.

9. The method of claim 7, further comprising regulating the heating of the substrate by controlling the reaction.

10. The method of claim 7, wherein the reagents result in an exothermic reaction by hydration of a salt powder, oxidation of a metal, displacement of a less reactive metal, a salt forming neutralization reaction between an acid and base, or combinations thereof.

11. The method of claim 7, wherein the one or more reagents comprise a calcium oxide powder.

12. The method of claim 7, wherein activating the heat source is achieved mechanically, physically, chemically or combinations thereof.

13. The method of claim 12, wherein the activation comprises hydrating the reagents to generate heat.

14. The method of claim 1, wherein the substrate comprises a solid phase extraction matrix, a filtration matrix, a paper, a foam, a membrane or combinations thereof.

15. The method of claim 1, wherein the substrate comprises a plurality of pores.

16. The method of claim 1, wherein the substrate comprises a polymeric material.

17. The method of claim 1, wherein the substrate has a thickness between 0.05 mm to 10 mm.

18. The method of claim 1, wherein the substrate is self-supported or encased in a frame.

19. The method of claim 1, wherein the substrate further comprises cell lysis reagents, biomolecule stabilizing reagents or combinations thereof.

20. A method of drying a biological sample, comprising:
disposing the biological sample on a substrate, wherein the substrate comprises a sample loading area and a reactor component comprising one or more reagents;
activating the one or more reagents to initiate an exothermic reaction;
heating the substrate at about 95° C.; and
drying the biological sample disposed on the substrate in less than about 2 minutes.

21. The method of claim 20, wherein the step of activating the one or more reagents is achieved by hydrating the substrate, aerating the substrate or adding one or more reagents to the substrate.

22. The method of claim 20, wherein the biological sample comprises proteins, peptides, nucleic acids or combinations thereof.

23. The method of claim 20, wherein the biological sample comprises nucleic acids comprising deoxyribonucleic acids (DNAs) or ribonucleic acids (RNAs).

24. The method of claim 20, wherein the one or more reagents are caused to initiate an exothermic reaction by hydration of a salt powder, oxidation of a metal, displacement of a less reactive metal, a salt forming neutralization reaction between an acid and base, or combinations thereof.

* * * * *